United States Patent
Turng et al.

(10) Patent No.: US 11,339,267 B2
(45) Date of Patent: May 24, 2022

(54) GREEN FABRICATION OF POLYTETRAFLUOROETHYLENE AND EXPANDED POLYTETRAFLUOROETHYLENE AND USES THEREOF

(71) Applicant: Wisconsin Alumni Research Foundation, Madison, WI (US)

(72) Inventors: Lih-Sheng Turng, Madison, WI (US); Yiyang Xu, Madison, WI (US); Yu-Jyun Lin, Madison, WI (US); Dong-Fang Wang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 171 days.

(21) Appl. No.: 16/744,505

(22) Filed: Jan. 16, 2020

(65) Prior Publication Data

US 2020/0231775 A1    Jul. 23, 2020

Related U.S. Application Data

(60) Provisional application No. 62/795,116, filed on Jan. 22, 2019.

(51) Int. Cl.
| | |
|---|---|
| *C08J 9/28* | (2006.01) |
| *A61L 27/16* | (2006.01) |
| *A61L 27/56* | (2006.01) |
| *C08J 3/09* | (2006.01) |

(52) U.S. Cl.
CPC .............. *C08J 9/286* (2013.01); *A61L 27/16* (2013.01); *A61L 27/56* (2013.01); *C08J 3/092* (2013.01); *C08J 2201/03* (2013.01); *C08J 2201/0502* (2013.01); *C08J 2327/18* (2013.01)

(58) Field of Classification Search
CPC ........ C08J 9/286; C08J 3/092; C08J 2201/03; C08J 2201/0502; C08J 2327/18; C08J 2203/12; C08J 9/125; C08J 9/142; C08J 2203/10; C08J 2203/182; C08J 2207/10; A61L 27/16; A61L 27/56; A61L 17/04; A61L 27/507; A61L 27/54; A61L 31/048; A61L 31/146; A61L 31/16
See application file for complete search history.

(56) References Cited

U.S. PATENT DOCUMENTS

| | | | | |
|---|---|---|---|---|
| 4,877,661 A | * | 10/1989 | House | ................... B29C 55/005 |
| | | | | 428/34.9 |
| 6,218,000 B1 | * | 4/2001 | Rudolf | .............. B01D 39/1692 |
| | | | | 264/122 |
| 2006/0147665 A1 | * | 7/2006 | Duran | ..................... C08L 27/18 |
| | | | | 428/36.9 |
| 2011/0171403 A1 | * | 7/2011 | Tabata | .................. C08F 114/26 |
| | | | | 428/35.5 |

* cited by examiner

Primary Examiner — Irina S Zemel
(74) Attorney, Agent, or Firm — Stinson LLP

(57) ABSTRACT

Green, fast and easy evaporating organic solvent for use as a lubricant in the processing of polytetrafluoroethylene (PTFE) and expanded polytetrafluoroethylene (ePTFE) products and processes of using the solvents to fabricate the products are disclosed herein. The products can be used in the field of bio- and medical applications, such as for use in vascular grafts, cardiovascular and soft tissue patches, facial implants, surgical sutures, and endovascular prosthesis, and for any products known in the aerospace, electronics, fabrics, filtration, industrial and sealant arts.

17 Claims, 18 Drawing Sheets

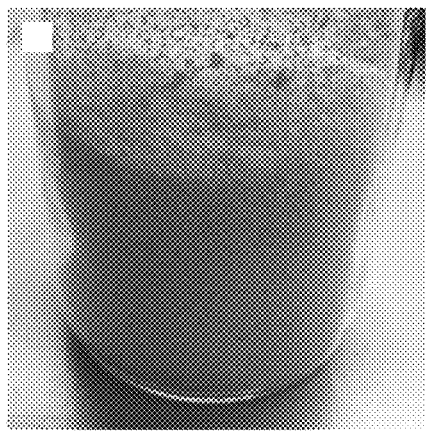
FIG. 1A
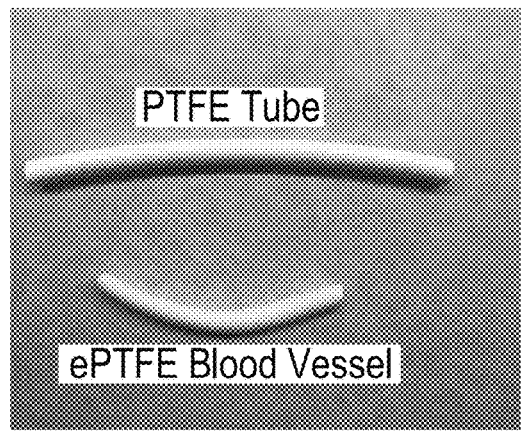
FIG. 1B
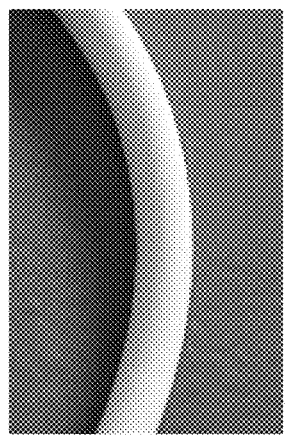
FIG. 1C
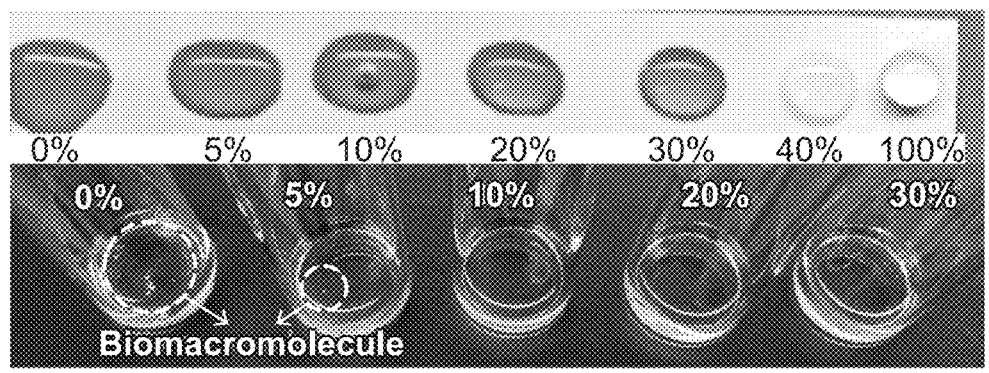
FIG. 2A
FIG. 2B

External surfaces

Internal surfaces

Before expansion

After expansion

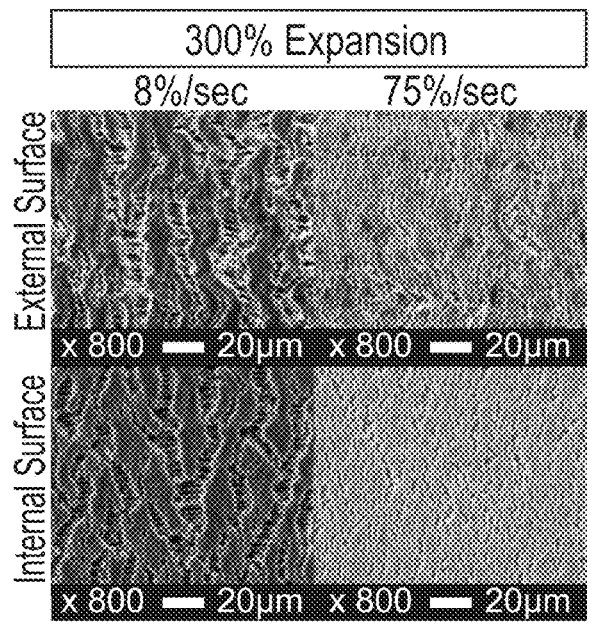 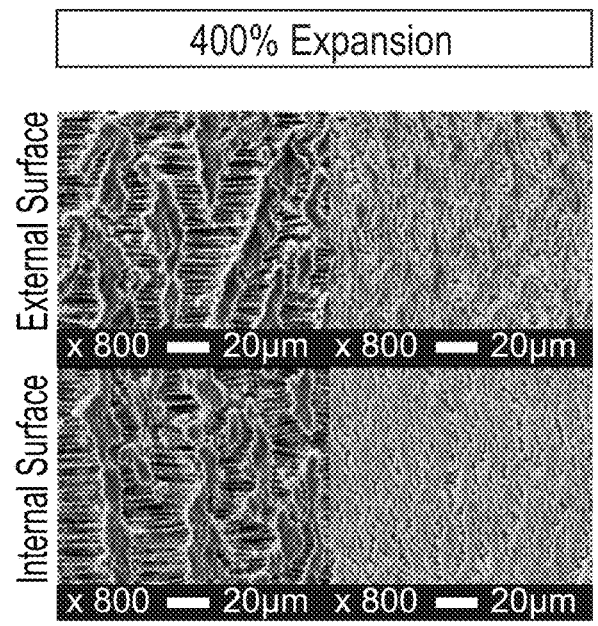
FIG. 19A    FIG. 19B
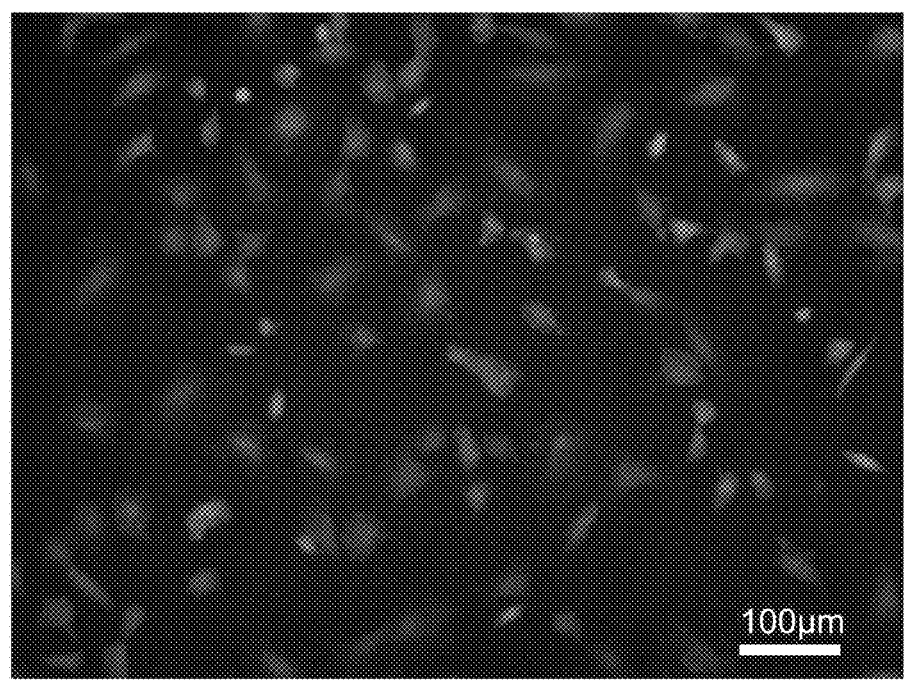
FIG. 20

GREEN FABRICATION OF POLYTETRAFLUOROETHYLENE AND EXPANDED POLYTETRAFLUOROETHYLENE AND USES THEREOF

CROSS-REFERENCE TO RELATED APPLICATION

This application claims priority to U.S. Provisional Patent Application Ser. No. 62/795,116, filed Jan. 22, 2019, which is hereby incorporated by reference in its entirety.

STATEMENT OF GOVERNMENT SUPPORT

This invention was made with government support under U01HL134655 awarded by the National Institutes of Health (NIH). The government has certain rights in the invention.

BACKGROUND OF THE DISCLOSURE

The present disclosure relates generally to the use of alternative lubricants, and in one particular embodiment, ethanol, as a green, fast and easy evaporating lubricant for processing polytetrafluoroethylene (PTFE) and expanded polytetrafluoroethylene (ePTFE), thereby enhancing the safety and utility of PTFE and ePTFE products. Additionally, the processes of the present disclosure allow the PTFE and ePTFE products to be modified with added functional biomolecules. These products can be used in the field of bio- and medical applications, such as for use in vascular grafts, cardiovascular and soft tissue patches, facial implants, surgical sutures, and endovascular prosthesis.

Polytetrafluoroethylene (PTFE) possesses a number of special properties such as a low dielectric constant (i.e., good electrical insulator), high thermal resistance, low coefficient of friction, low flammability, resistance to UV light, hydrophobicity, oleophobicity, and chemical inertness. ePTFE possesses other attractive attributes such as porosity, air permeability and tunable strength. Due to its biocompatibility and inertness, ePTFE has also been particularly useful in medical implants such as vascular grafts.

Due to its inability to flow, even when melted, and inability to be dissolved, however, traditional processing of PTFE requires industrial lubricants (lubricating agents) such as Isopar G and Naphtha as processing aids. These traditional lubricants are slightly toxic, flammable and non-biofriendly. Further, the evaporation of the lubricant requires special handling and venting to avoid air pollution or explosion. In the residual environment, the material could lead to respiratory disease or even cancer.

The above shortcomings limit the applications of PTFE and/or require secondary processing to thoroughly remove the lubricant. Accordingly, green fabrication of PTFE and ePTFE remains a challenging and urgent need in the industry. It would be further advantageous if the processing allowed for bio-functional materials to be added to the final products to provide additional desired functions.

BRIEF DESCRIPTION OF THE DISCLOSURE

The present disclosure is directed to the use of alternative lubricants, and in particular, organic solvents such as lower alkyl ($C_1$-$C_{10}$) alcohols (e.g., ethanol), as lubricants for processing polytetrafluoroethylene (PTFE) and expanded polytetrafluoroethylene (ePTFE). The use of these alternative lubricants eliminates the serious drawbacks and safety concerns associated with traditional lubricants, enhancing the safety and utility of PTFE and ePTFE products, especially in the field of bio- and medical applications. Additionally, the processing methods of the present disclosure allow biomodification of the products through the addition of biofunctional molecules. These biofunctional molecules provide various additional desired functions to the end products without compromising the lubricating function of the lubricant during processing. In particular embodiments, the biofunctional materials and other functional additives are included during the processing of the PTFE and/or ePTFE materials.

Accordingly, in one aspect, the present disclosure is directed a process for preparing an extruded product. The process includes: blending a polytetrafluoroethylene (PTFE) powder with an organic solvent to form a blend; preforming the blend; extruding the preformed blend to form a product; and evaporating the solvent from the extruded product. In some embodiments, the method further comprises sintering the heated extruded product. Typically, the organic solvent is a lower alkyl ($C_1$-$C_{10}$) alcohol.

In another aspect, the present disclosure is directed to a process for preparing an extruded product with an additional pretreatment of the polytetrafluoroethylene (PTFE) powder with a target additive, such as a biofunctional molecule or other functional additive. The process of this aspect includes: dissolving a target additive into an organic solvent to form a target-solvent solution; immersing a polytetrafluoroethylene (PTFE) powder in the target-solvent solution to form a blend; preforming the blend; extruding the preformed blend to form a product; and evaporating the target-solvent solution from the extruded product. In some embodiments, the method further comprises sintering the heated extruded product.

In an alternative embodiment, the present disclosure is directed to a process for preparing an extruded product with an additional post-treatment of the PTFE with a target additive, such as a biofunctional molecule or other functional additive. The process includes: dissolving a target additive into an organic solvent to form a target-solvent solution; immersing a sintered extruded polytetrafluoroethylene (PTFE) product in the target-solvent solution to form a wetted PTFE product; and evaporating the target-solvent solution from the extruded product, which leaves the target additive inside the PTFE.

In another aspect, the present disclosure is further directed to expanding the extruded product for use in products such as vascular grafts, cardiovascular and soft tissue patches, facial implants, surgical sutures, and endovascular prosthesis, and for any products known in the aerospace, electronics, fabrics, filtration, industrial and sealant arts.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 1A-1C depict the use of ethanol as a lubricant for processing PTFE and ePTFE. FIG. 1Aa shows wettability of ethanol. FIG. 1B depicts ethanol-assisted PTFE/ePTFE fabrication. FIG. 1C depicts PTFE made with Naphtha.

FIGS. 2A & 2B depict dissolving biomolecules in the ethanol/water-lubricant mixture. Numbers in percentage indicated the weight percent of water.

FIGS. 19A & 19B depict intermodal distances of the ePTFE blood vessel expanded at 40° C. at 300% expansion ratio (FIG. 19A) and 400% expansion ratio (FIG. 19B) with varied expansion rates.

FIG. 20 depicts the cultured endothelial cells on the ePTFE blood vessel substrate on Day 3.

DETAILED DESCRIPTION

Figure 3:
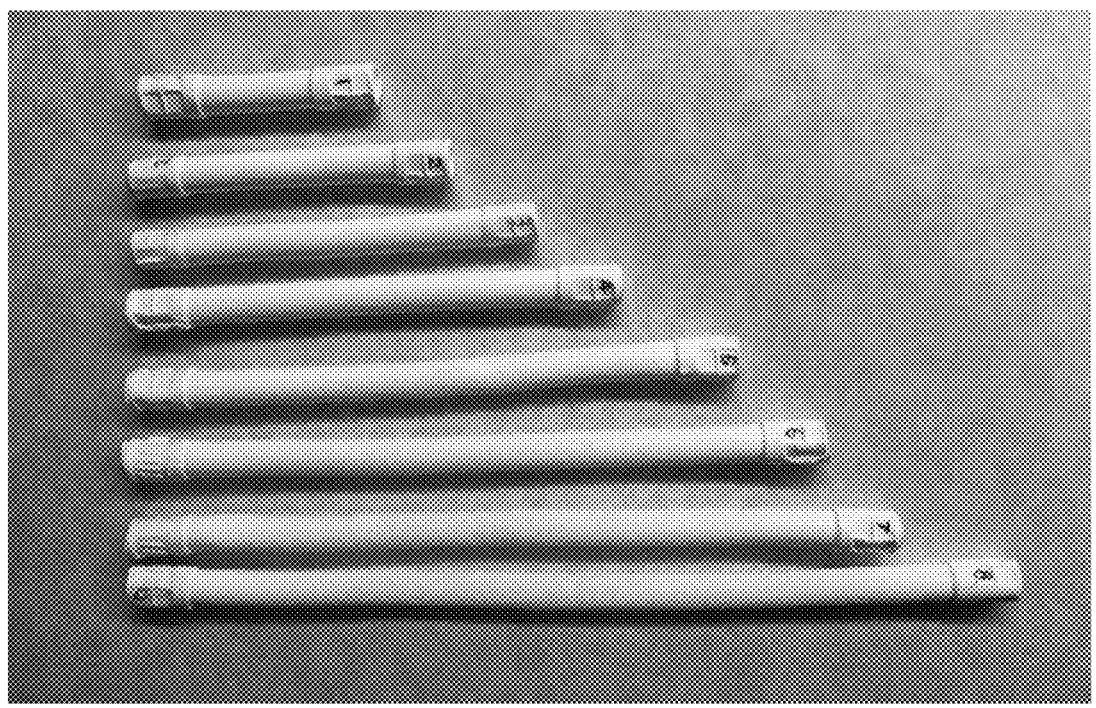
FIG. 3 depicts appearances of expanded PTFE tubes. The tubes showed a rough surface when the expansion ratio is larger than 400%.

Unless defined otherwise, all technical and scientific terms used herein have the same meaning as commonly understood by one of ordinary skill in the art to which the disclosure belongs.

Generally, it has recently been found that organic solvents, such as biocompatible lower alkyl ($C_1$-$C_{10}$) alcohols (e.g., methanol, ethanol, isopropanol, and the like), can behave as alternative processing lubricants for processing polytetrafluoroethylene (PTFE) and expanded polytetrafluoroethylene (ePTFE). For example, these lubricants allow for good wettability on PTFE powders and are fast and easily removed through evaporation. In contrast to traditional lubricants (e.g., Naphtha), which are flammable, polluting, toxic and have been linked to latent diseases, ethanol is non-toxic and non-corrosive, thereby being a green lubricant that can further enhance the safety and utility of finished PTFE and ePTFE products.

As shown in FIG. 1A, ethanol, dyed by a red colorant, has very good wettability on PTFE powders. The resulting paste-extruded PTFE and ePTFE tubes using ethanol as a lubricating agent (compare FIGS. 1B & 1C) showed that ethanol works as good as the traditional industrial lubricant (e.g., Naphtha) in PTFE and ePTFE processing. Further, due to its low boiling point, ethanol can evaporate quickly.

Generally, the processes of the present disclosure include (1) mixing the PTFE powders with organic solvents used as lubricants (e.g., lower alkyl alcohols) to form a blend; (2) preforming the blend; (3) extruding the preformed blend to form a product; and (4) evaporating the solvents from the extruded product. When it comes to ePTFE fabrication, the PTFE extrudate should be expanded prior to sintering.

Suitable organic solvents for use as the alternative lubricant or in a mixture for use as the alternative lubricant include, for example, lower alkyl alcohols (e.g., methanol, ethanol, isopropanol, propan-2-ol, butan-1-ol, and the like), acetic acid, ethyl acetate, acetonitrile, chloroform, benzene, methylbenzene, dimethylbenzene, acetone, 2-butanone, cyclopentanone, pentane, n-hexane, cyclohexane, heptane, dichloromethane, dichloroethane, trichloroethane, tetrachloromethane, tetrachloroethane, trimethylpentane, 1,4-dioxane, chloroform, ether, dimethyl sulfoxide (DMSO), dimethylformamide (DMF), tetrahydrofuran (THF), and combinations thereof. The organic solvents can further be combined with a carrier such as water, and the like, to form a solvent mixture.

The choice of organic solvent and/or solvent mixture will be dependent on the type of solvent, and, if a biofunctional molecule or other functional additive is to be included with the PTFE or ePTFE product, the type, amount and/or solubility of biofunctional molecule or other functional additive.

For blending, it is generally suitable for the organic solvent to be present in the blend in an amount of from about 10% to 30% by weight of the total blend. The organic solvent and PTFE powders are blended using any means in the art for blending, and typically, are blended for a rolling time of from about 30 minutes to about 120 minutes and an aging time of from about 30 minutes to about 48 hours. Aging is typically conducted at a temperature of 40° C. to keep the blend at a lower temperature than the boiling point of the solvent for a period of time, which facilitates uniform wetting.

In further embodiments, it has been advantageously found that the solvents described herein can be used as a carrier for biofunctional molecules and other target materials to allow for introduction of the target materials into the final extruded product. Particularly, the polytetrafluoroethylene (PTFE) powder or final sintered extruded product is pre- or post-treated with a target material during the mixing of the PTFE with the solvents (with or without the addition of a carrier (e.g., water)).

When the target material is added as a pretreatment, the pretreatment process generally includes: dissolving a target material in the organic solvent to form a target-solvent solution; and then immersing the polytetrafluoroethylene (PTFE) powder in the target-solvent solution to form the blend, which is then dried by evaporating the organic solvent, preformed, extruded to form a product including the target material. Alternatively, the target material can be added as a post-treatment to a sintered extruded PTFE product. In the post-treatment process, the sintered extruded product is wetted (e.g., immersed) in the target-solvent solution to wet the product, and then dried by evaporating the organic solvent from the product, which leaves the target material inside the PTFE product.

Historically, PTFE is difficult to modify because of its chemical inertness. Previous solutions for improving PTFE's behavioral properties without changing its chemical structure have included surface coating, chemical bonding, and plasma treatment. Surface coating, however, cannot reach deep inside the PTFE powder and resulting products. Chemical bonding requires toxic chemicals and complex procedures. And, plasma treatment is greatly limited by the resulting PTFE product's geometry. By contrast, using the methods of pretreatment as disclosed herein, the target material reaches into the powders and the surface of the PTFE powder can be completely uniformly coated by a target material. Further, as verified by subsequent expansion experiments and characterization, all of the target material was evenly distributed over the PTFE powder. And, the processability of the pretreated PTFE powder was not impaired by this pretreatment process, such that an expanded porous PTFE (i.e., ePTFE) could be produced.

Similarly, it has been found that, when post-treated with a target material using the processes of the present disclosure, the PTFE product can be uniformly coated with the target material.

In one embodiment, the process generally first involves dissolving a target material in an organic solvent to form a target-solvent. Specifically, target materials may include biofunctional materials (e.g., dopamine, heparin, growth factors (e.g., EGF, FGF, NGF, PDGF, VEGF, IGF, GMCSF, GCSF, TGF, Erythropieitn, TPO, BMP, HGF, GDF, Neurotrophins, MSF, SGF, and the like, and combinations thereof), induction factors for stem cell differentiation, cell growth inhibitors, proteins, enzymes, and the like, and combinations thereof), therapeutics (e.g., anticoagulant: heparin, salicin, and bivalirudin; anticancer agents: nimustine hydrochloride, doxifluridine, and daunorubicin; anti-inflammatory agents: aspirin, cephradine, and cilastatin; and antibiotic agents: penicillin, cephalosporins, and erythromycin, natural compounds (e.g., vitamins), aesthetic agent (e.g., pigments), and the like, and combinations thereof that can be dissolved in the organic solvent and, after the evaporation of the organic solvent, remain inside and uniformly on the surface of the final extruded product, endowing them with specific desirable biofunctional, physical and aesthetic properties.

When dissolved in the organic solvent, the target materials are typically present in an amount of from about 0.1% by weight to about 5% by weight total material/organic solvent mixture. Advantageously, with the use of the organic solvents in the present disclosure, the target material(s) can be dissolved in the solvents at room temperature.

As noted above, in some embodiments, it is suitable to include a carrier (e.g., water) with the organic solvent to form a carrier mixture to dissolve the target material. The addition of water (or other bio-friendly carrier) can increase the solubility of target molecules such as biofunctional molecules without compromising the lubricating function of the organic solvent (see FIGS. 2A & 2B). The higher the water ratio, the more biofunctional molecules the organic solvent could carry. However, if the water ratio is too high, the organic solvent mixture cannot wet the PTFE powders, resulting in processing failure. Typically, when water is used with the organic solvent, the solvent/water mixture has a ratio of solvent:water of from about 10:90 to about 100:0, more suitably, the ratio is larger than 50:50; and even more suitably, the ratio is 70:30.

The target material is dissolved in the organic solvent or solvent mixture for a period of from about 0.5 hour to about 2.0 hours. Typically, the target material is dissolved in room temperature solvent or mixture with a mixing speed of from about 60 rpm to about 200 rpm under normal atmosphere.

Once the target material is dissolved, the polytetrafluoroethylene (PTFE) powder or sintered extruded PTFE product is immersed in the target-solvent solution at room temperature for a period of from about 0.5 hours to about 2.0 hours. Typically, when used as a pretreatment, the PTFE powder is blended into the target-solvent solution with any known means of mechanical blending at a speed of about 60 rpm to about 200 rpm under normal atmosphere. By way of example, the PTFE powder can be magnetically stirred into the target-solvent solution. In one embodiment, from about 0.2 wt % to about 40 wt % of the PTFE powder is immersed in the target solvent solution.

By way of one suitable embodiment, the processes of the present disclosure have been found to be effective for drug loading. While untreated ePTFE has poor biocompatibility, drug-loaded ePTFE made via the processes disclosed herein, exhibit greatly enhanced biocompatibility (see Example 9), which could provide applications in the medical and food industries.

Once blended, the blend is preformed at room temperature (23° C. +/−2° C.). That is, the blend is compressed and compacted with a defined pressure and compression rate. Preforming has two functions: first, it gives shape and second, it removes any air pockets from within the material. The maximum pressure depends on the consistence of the powder and presence of any additional ingredients in the blend (e.g., biomolecules). Typically, the pressure ranges from about 1 MPa to about 30 MPa, and suitably about 2 MPa. The pressure is typically maintained for a period of from about 0 minutes to about 120 minutes, including from about 0 to about 60 minutes.

Following preforming, the preform blend is extruded through any extruder known in the extruding arts to give the final product its shape. In some suitable embodiments, the preform blend is extruded in a ram extruder.

The organic solvent is then evaporated from the extrudate by heating or ventilation. Conventionally, to evaporate the solvent, the extrudate had to be heated to a temperature of from 60° C. to about 200° C. for a period of from about 0.5 minutes to about 120 minutes. With the use of lower boiling point organic solvents as lubricants, the process of the present disclosure can evaporate the organic solvent at room temperature for a period of from about 1 hour to about 96 hours, including from about 1 hour to about 72 hours. This proves beneficial as it is more cost effective and efficient. Further, if target materials are introduced in the products, the lower evaporation temperature prevents degradation of some target materials (e.g., biofunctional molecules) and/or their functional properties that they provide the products.

When appropriate, in some embodiments, the extruded product may then be sintered at a temperature of from about 360° C. to about 400° C. for a period of from about 10 seconds to about 10 minutes to provide final mechanical properties.

In some embodiments, the extruded product is expanded into a desired size and shape prior to sintering. Expansion can be at a typical expansion temperature (200-300° C.), however, it has advantageously been found that organic solvents used in the present disclosure as lubricants, such as ethanol, have a lower boiling point, and thus, can be expanded at lower temperatures, for example from about 25° C. to about 340° C., including from about 25° C. to about 300° C., including from about 30° C. to about 60° C., and including about 37° C. Further, suitable stretch rates include from about 1 mm/min to about 5000 mm/min, including from about 1 nm/min to about 1000 nm/min.

Maximum expansion will vary depending on the specific application. Typically, however, maximum expansion ratios of the PTFE products are about 800%, more typically, the expansion ratio is from about 100% to about 800%, and more typically still, about 400%. It has been found (as shown in FIG. 3), that PTFE tubes prepared and expanded using the processes of the present disclosure show a rough surface when the expansion ratio is larger than 400%.

Suitably, the PTFE products prepared by the processes of the present disclosure can be used for any products known in the aerospace, electronics, fabrics, filtration, industrial and sealant arts. It has been found herein that the products are particularly useful in medical implants such as vascular grafts, cardiovascular and soft tissue patches, facial implants, surgical sutures, and endovascular prostheses. As shown in FIG. 20, endothelial cells grew very well on the as fabricated ePTFE substrate, which could facilitate rapid endothelialization for vascular graft applications.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

Example 1

In this Example, a PTFE tube was fabricated using the process of the present disclosure.

Figure 4:
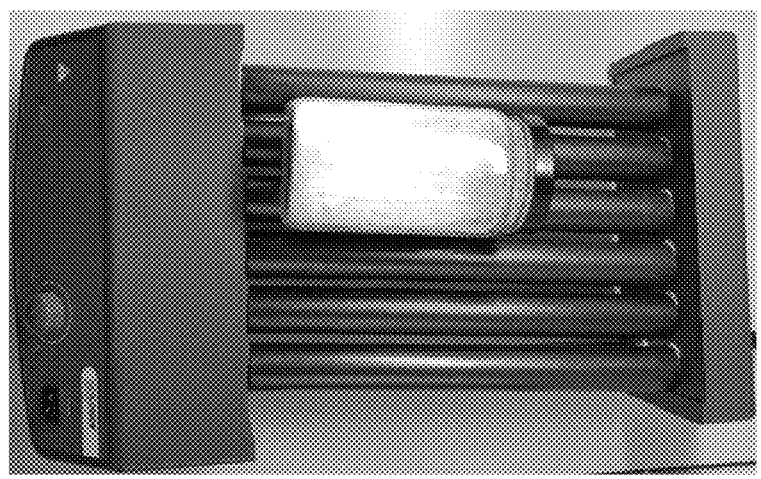
FIG. 4 depicts rolling of the blends of PTFE powders from Example 1.

80 grams of PTFE powders (F301 from Daikin) were blended with 20 grams of ethanol in a glass bottle. Roll the bottle at room temperature for 30 minutes at a speed of 10 rpm (shown in FIG. 4). The blends were then placed in an oven for 1 hour at 40° C.

Figure 5:
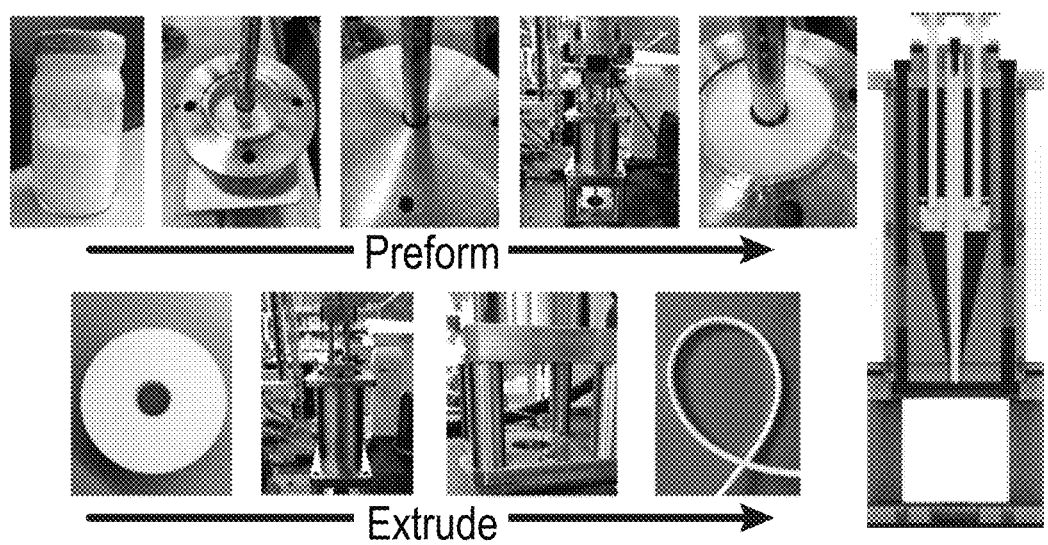
FIG. 5 depicts preforming and extruding a PTFE tube as fabricated in Example 1.

The aged blends were loaded into a barrel to make a preform using a pressure of 2 MPa (shown in FIG. 5 at "Preform"). When the pressure reached 2 MPa, it was maintained for 10 minutes. All the temperatures were room temperature unless otherwise specified. After being released from the barrel, the billet was extruded into a 6 mm I.D. and 8 mm O.D. tube using the ram extruder having a reduction ratio of about 100:1 in cross sectional area from billet to the extruded tube, which was shown in FIG. 5 at "Extruding". The geometry of the ram extruder is also shown in FIG. 5.

The as extruded tube then was sintered at 380° C. for 2 minutes to enhance its mechanical performance.

Example 2

In this Example, an ePTFE tube was fabricated using the process of the present disclosure.

Figures 6A, 6B:
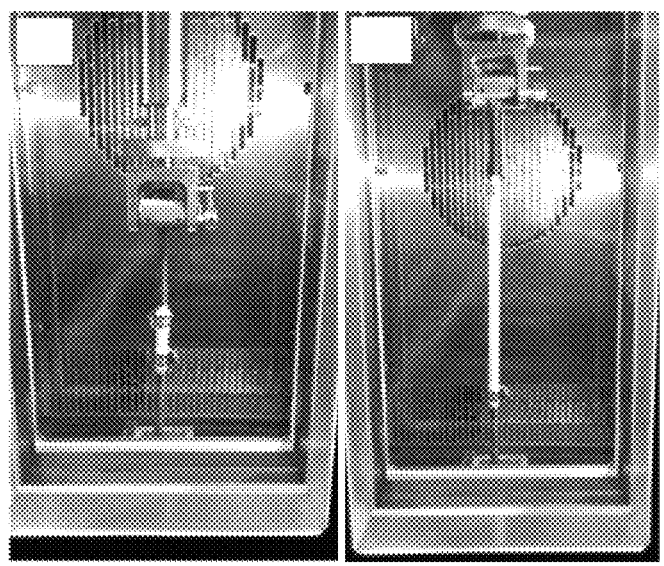
FIG. 6A depicts removal of residual ethanol during the fabrication process of an ePTFE tube in Example 2.
FIG. 6B depicts expansion of the pre-sintered PTFE tube during the fabrication process in Example 2.

The PTFE tube used in this Example was made following the procedures described above in Example 1, except that the tube was pre-sintered. Before expansion, the tube was placed in the oven for 5 minutes at 100° C. for complete ethanol evaporation, which is shown in FIGS. 6A & 6B. Then the tube was stretched 8 times longer at 200° C. with a stretching rate of 1000 mm/min, which is shown in FIG. 6B. After the expansion, the stretched tube was heated up to 380° C. for 40 seconds.

Example 3

In this Example, an ePTFE tube was fabricated with the addition of biomolecules using the process of the present disclosure.

The organic solvent used in this Example was an ethanol/water mixture having a water ratio of 30% by weight mixture; that is an ethanol/water ratio of 70:30. Before blending with PTFE powders, 0.5% by weight of dopamine was dissolved in the ethanol/water mixture. The tubing process was the same as described above for Examples 1 & 2.

Evaporation of ethanol was done at room temperature through venting for 24 hours. Expansion was conducted at 40° C. instead of 200° C. These variations were to keep biomolecules from being inactive or degrading. Beyond dopamine, heparin and other cell growth factors could also be added in PTFE/ePTFE products, which will confer diverse functions on the final tube products.

Example 4

In this Example, ePTFE blood vessels are fabricated using ethanol as a lubricant.

Figures 7A, 7B:
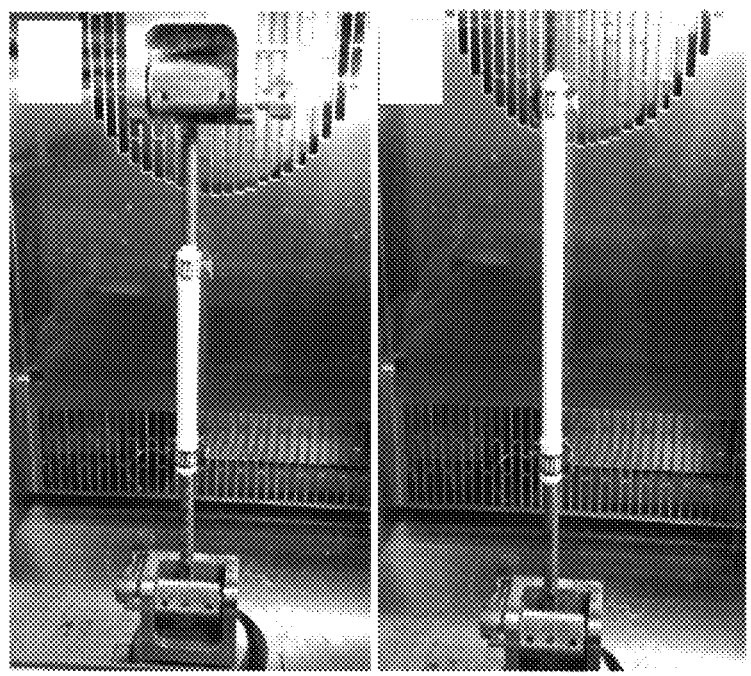
FIGS. 7A & 7B depict expansion of a PTFE tube to an expansion ratio of 400% (FIG. 7A) and 800% (FIG. 7B).

Initially, a PTFE tube (20 mm) was prepared and extruded as described in Example 2, using 18% by weight ethanol. The tube is then expanded in a chamber from Instron at a temperature of 200° C. and an expansion rate of 75%/second. The tube was expanded to an expansion of 400% (FIG. 7A) and 800% (FIG. 7B).

Example 5

Figure 8:
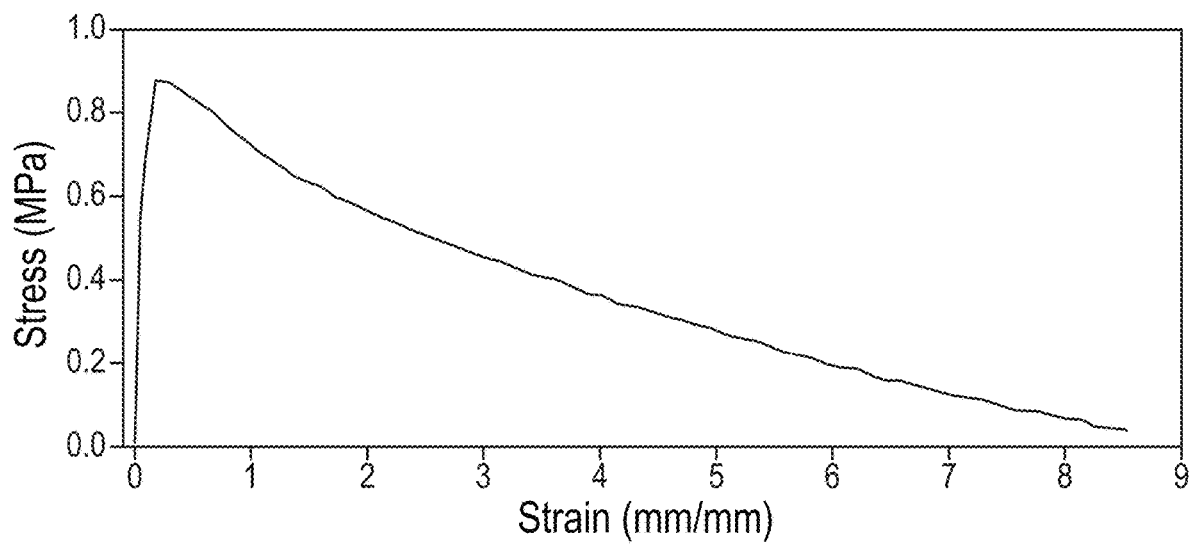
FIG. 8 depicts strain and stress curve during expansion. The maximum expansion ratio is around 850%.

In this Example, ePTFE blood vessels are fabricated using ethanol as a lubricant.

ePTFE tubes (20 mm) were prepared and extruded as described in Example 2, using 18% by weight ethanol. The tubes were then expanded in an environmental chamber from Instron at a temperature of 200° C. and an expansion rate of 150%/second to a maximum expansion of approximately 850%. FIG. 8 shows a strain and stress curve during expansion. The curves showed how PTFE responded to the applied deformation. Like other plastic material, the curve also exhibited a yielding point. After the yielding point, the stress began to decrease as the fibers-nodes structure (fibrillation) started to form. What is different from regular materials is that the ePTFE tube won't break suddenly. Instead, the stress continued to decay gradually, which was caused by ongoing fibrillation and gradual fracture of the fibers.

Example 6

In this Example, effects of expansion ratios and expansion rates were analyzed of the blood vessels fabricated in Example 5.

Figure 9:
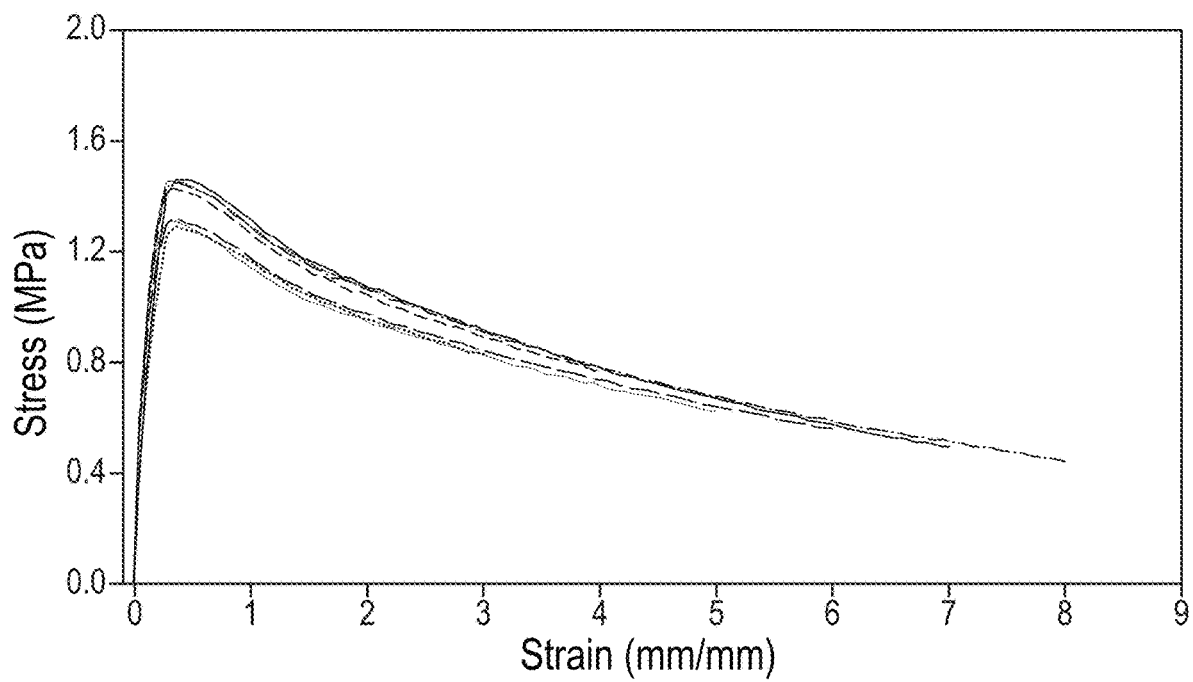
FIG. 9 depicts strain and stress curves with different expansion ratios.

As shown in FIG. 9, seven different ePTFE tubes prepared as described herein were expanded at different expansion ratios ranging from 100% to 800%. All the strain and stress curves showed similar elastic stage and yielding point.

Figure 10:
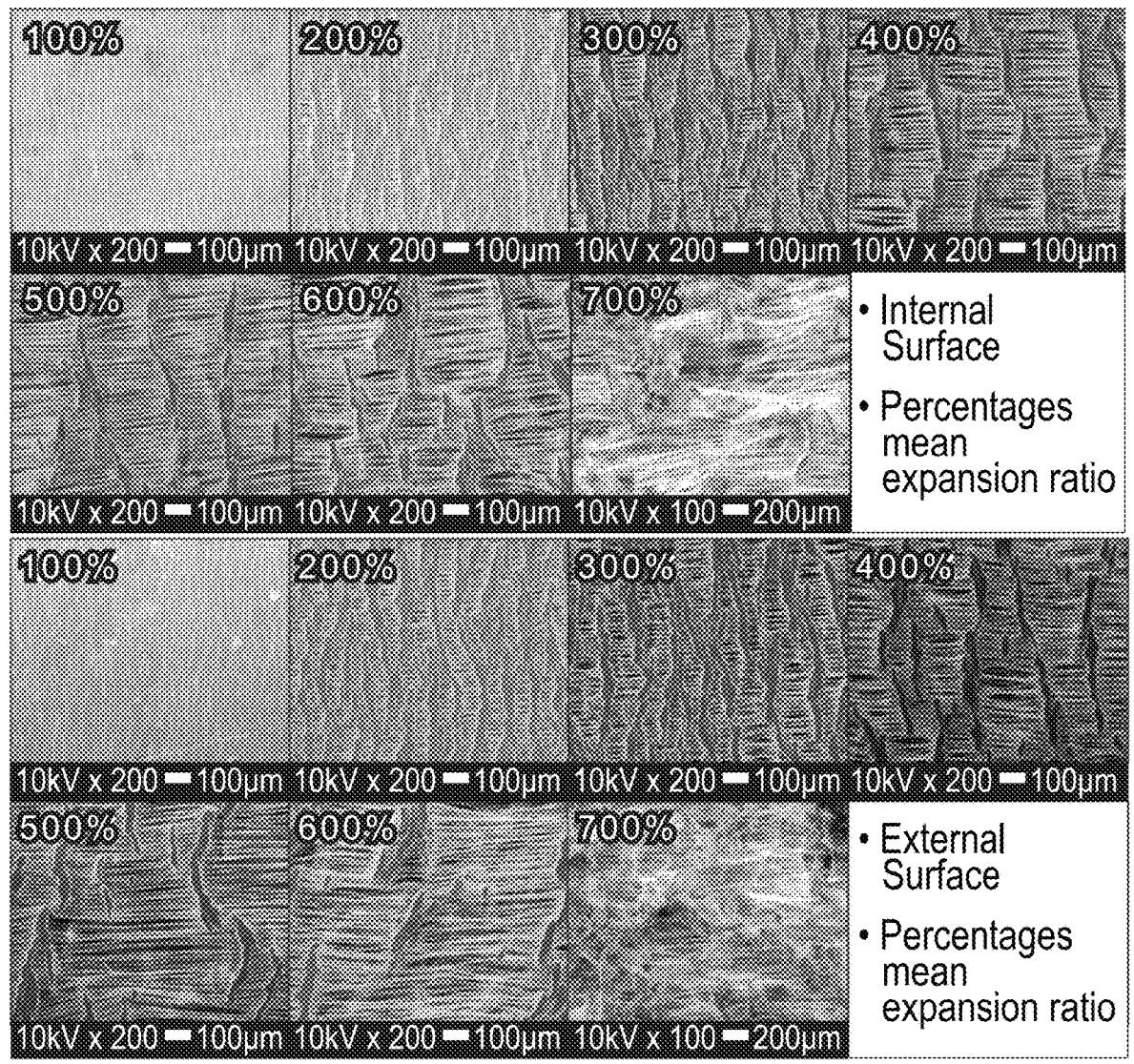
FIG. 10 depicts images of ePTFE external and internal surfaces expanded at various expansion ratios.
Figure 11A:
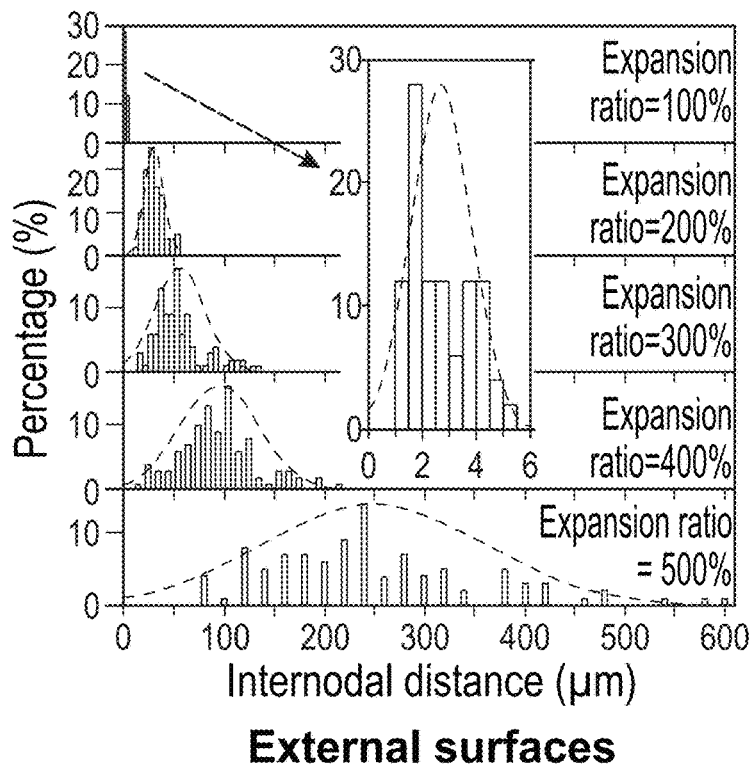
FIGS. 11A & 11B depict distribution of internodal distance of ePTFE blood vessels.
Figure 11B:
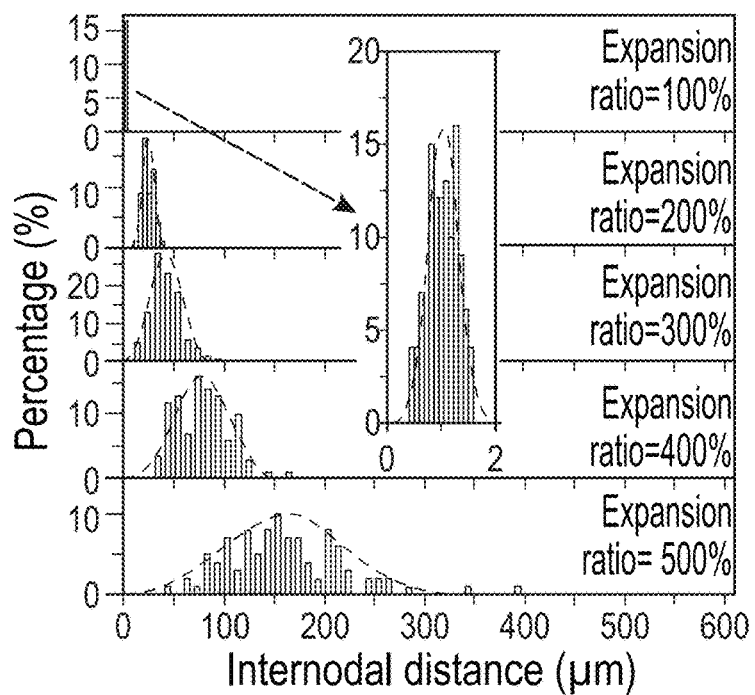
Figure 12:
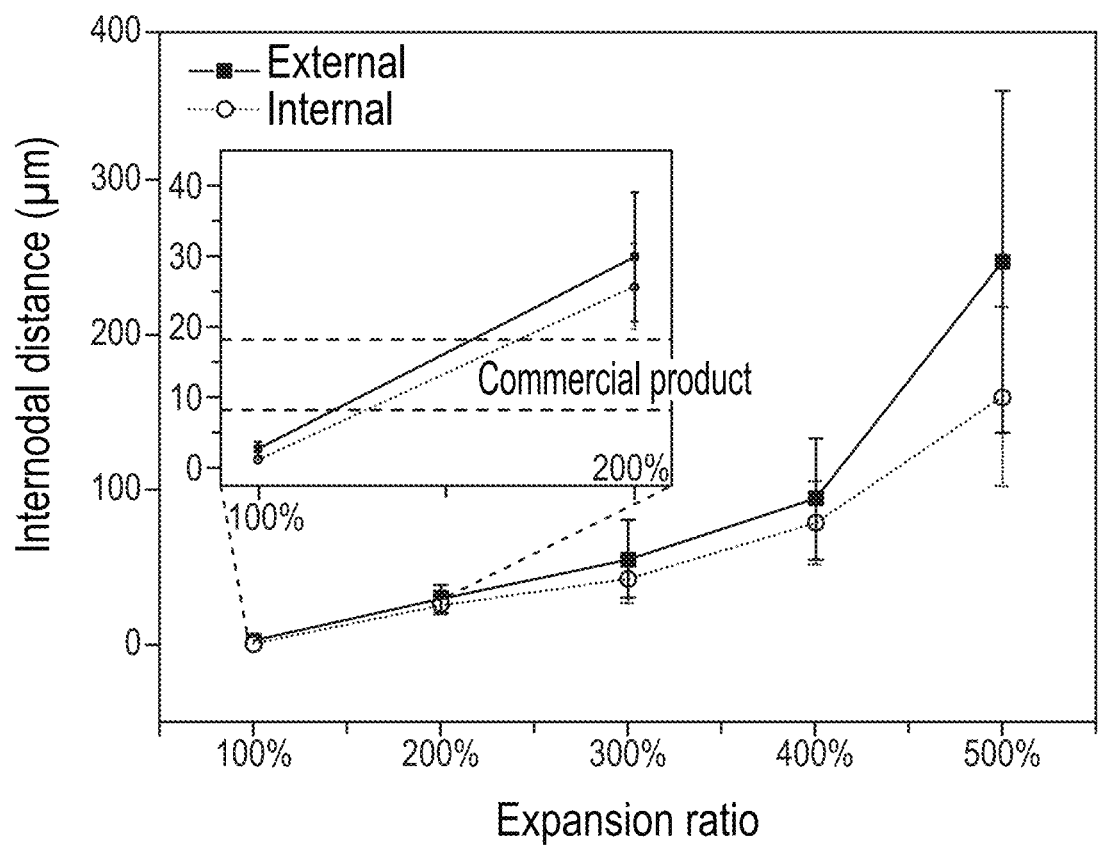
FIG. 12 depicts adjustable intermodal distance of ePTFE blood vessels.

Further, images were taken of ePTFE tubes expanded between 100% and 700% expansion ratios (see FIG. 10). Internodal distances were also analyzed (see FIGS. 11A & 11B and 12). With the increase of expansion ratio, the intermodal distances on both internal and external surfaces also increased. The intermodal distances on the external surface was always slightly larger than that on the internal surface. Based on the statistical result shown in FIG. 12, intermodal distances of the ePTFE tube could be tuned to meet different commercial needs. As a new method to quantify the extent of fibrillation, line density and line average of the tubes was proposed and analyzed. Line density, D, is calculated by:

$$D=(L_1+L_2+L_3)/L$$

Line average:

$$L_{ave}=(L_1+L_2+L_3)/3$$

Figure 13:
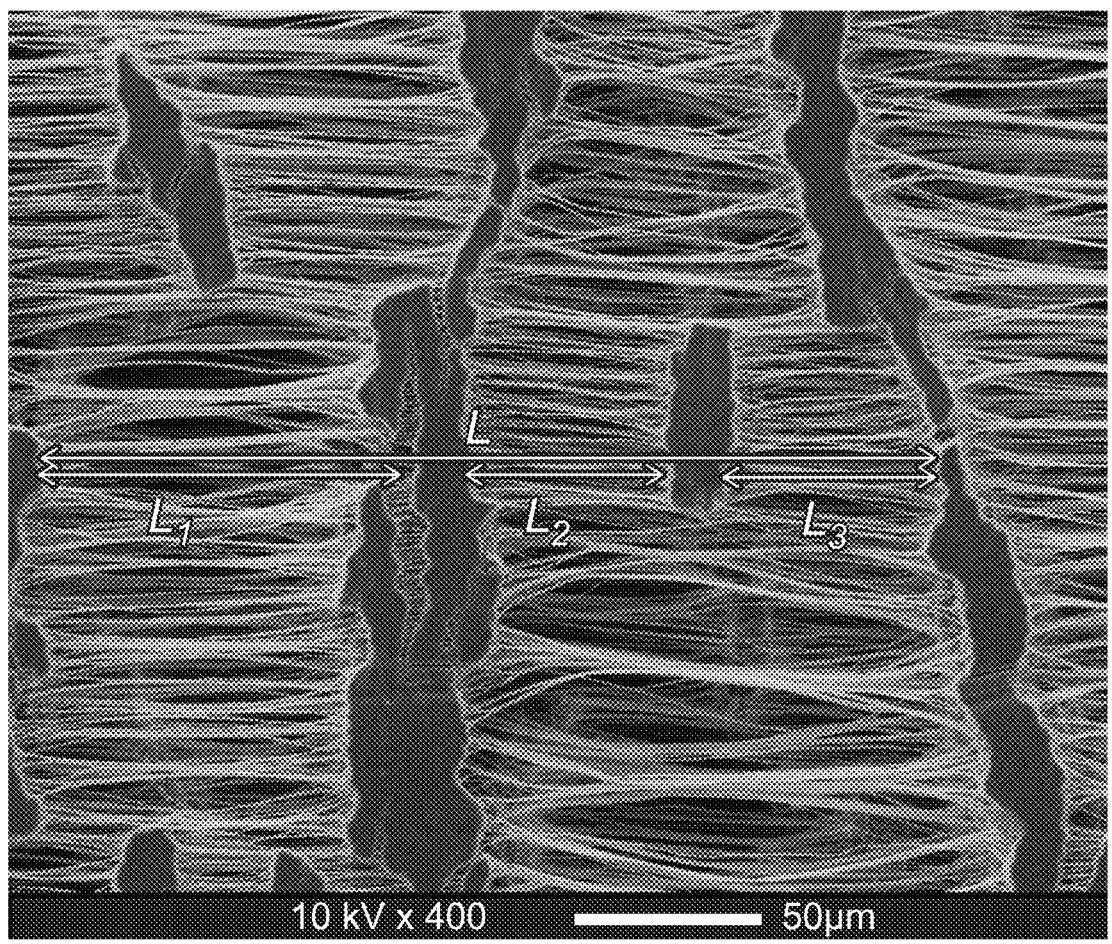
FIG. 13 depicts the quantification of ePTFE blood vessels by the introduction of line density and line average intermodal distance.
Figure 14A:
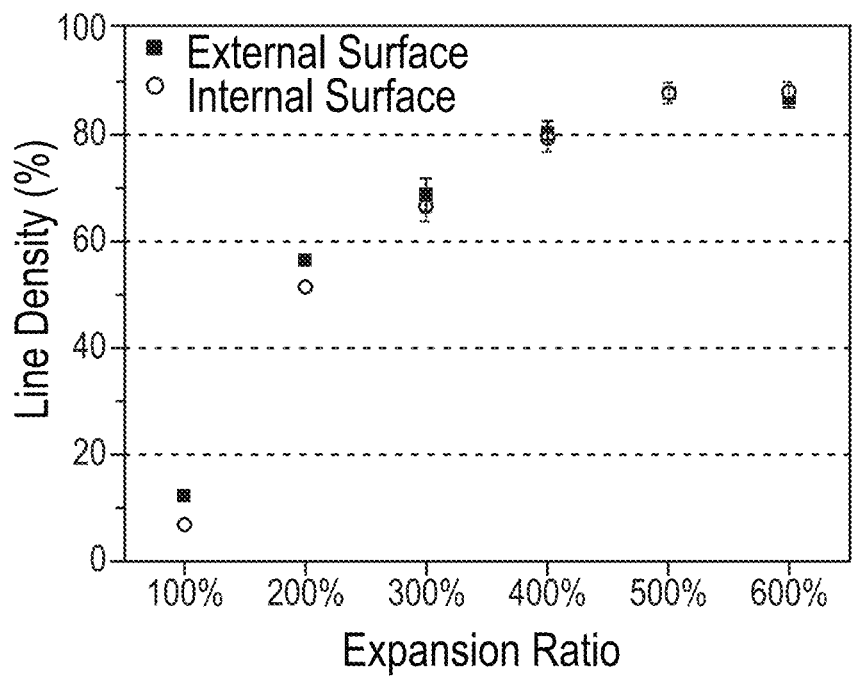
FIGS. 14A & 14B depict modified statistical results in the form of line density (FIG. 14A) and line average intermodal distance (FIG. 14B).
Figure 14B:
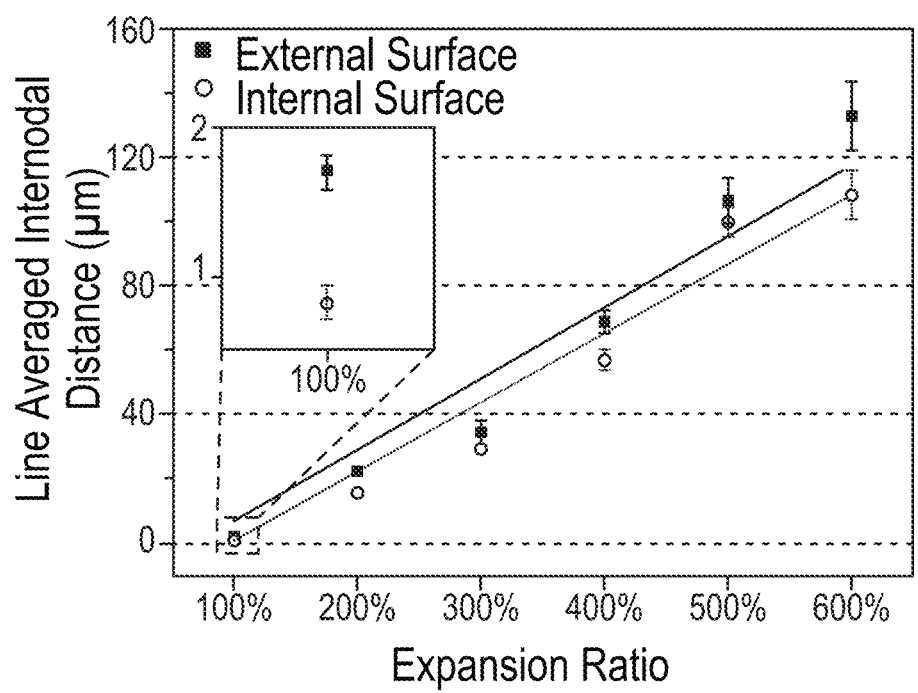

If the sampling length, L, is long enough, the calculated line density and line averaged intermodal distance provide meaningful and quantitative measures about the extents of expansion and fibrillation (see FIGS. 13 and 14A &14B).

Figure 15:
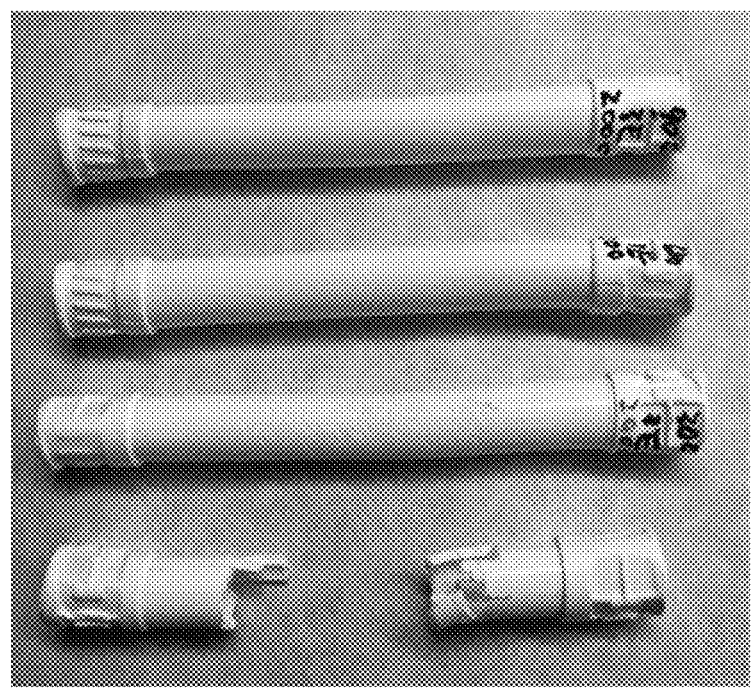
FIG. 15 depicts effect of expansion rate on ePTFE blood vessels' external surfaces (expansion rate from top to bottom are 75%/sec, 50%/sec, 25%/sec, and 8%/sec).
Figure 16:
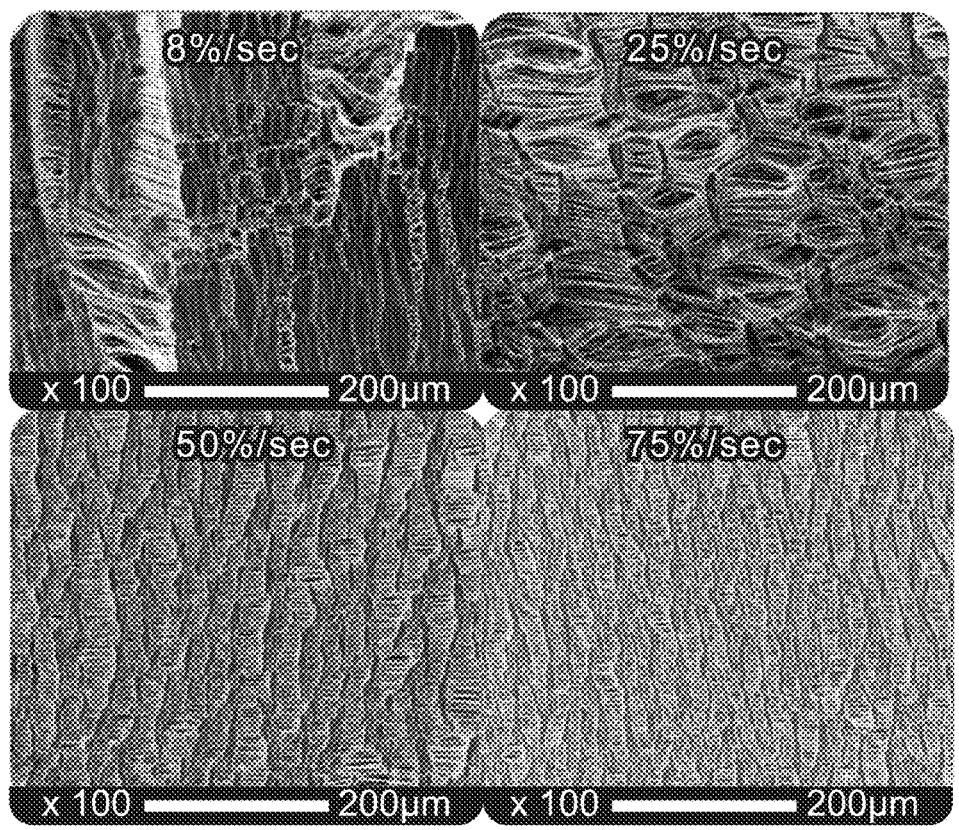
FIG. 16 depicts effect of expansion rate on ePTFE blood vessels' internal surfaces.
Figure 17A:
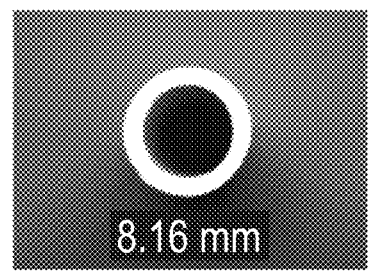
FIGS. 17A-17C depict wall thickness of ePTFE prior to (FIG. 17A & 17C) and after expansion (FIGS. 17B & 17C).
Figure 17B:
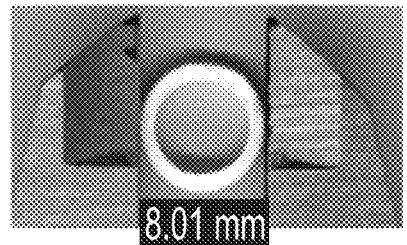
Figure 17C:
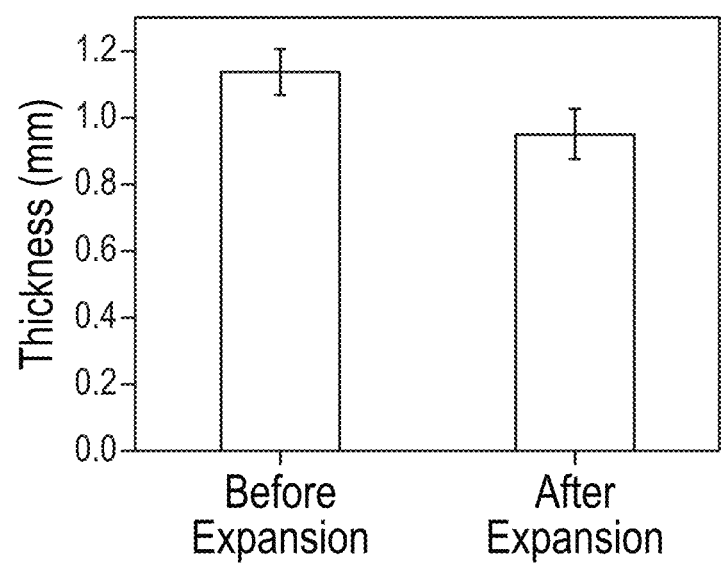

To analyze expansion rate on the tube, the tubes were expanded at an expansion ratio of 300%. As shown in FIG. 15, the higher the expansion rate, the smoother the surface of the tube. Moreover, the ePTFE tube turned unexpandable with the expansion rate being at 8%/sec or lower, which was caused by relaxation behavior of material. The intermodal distances matched with the surface roughness (see FIG. 16). Finally, as shown in FIGS. 17A-17C, there was uniform wall thickness prior to and after expansion.

Example 7

In this Example, ePTFE blood vessels are fabricated using ethanol as a lubricant.

ePTFE tubes (20 mm) were prepared and extruded as described in Example 2, using 18% by weight ethanol. The tubes were then expanded in an environmental chamber from Instron at a temperature of 40° C., using various expansion rates to an expansion of approximately 300%.

Figure 18A:
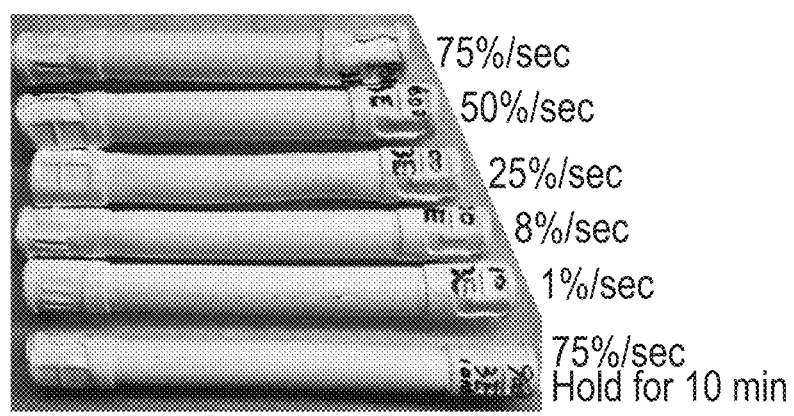
FIGS. 18A & 18B depict expansion of ePTFE blood vessels at 40° C. and various expansion ratios and varied shrinkage.
Figure 18B:
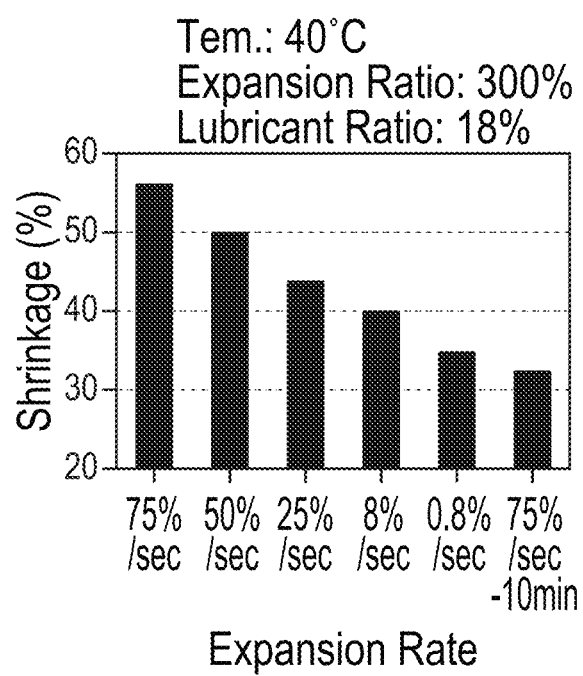

As shown in FIGS. 18A & 18B, at this expansion temperature, the tubes shrank back after being released from the tensile instrument due to the elasticity of PTFE. Accordingly, the process was amended to hold the tube at expansion for 10 minutes prior to releasing, which reduced shrinkage.

Further, the intermodal distances of the ePTFE tubes expanded at 40° C. were analyzed. The results are shown in FIGS. 19A & 19B. First of all, micro structures of the ePTFE tubes were the same as those expanded at 200° C. Secondly, when expanded at a lower temperature, a lower expansion rate helped increase the intermodal distances. This is because materials have a longer relaxation time at lower temperatures. Lowering the expansion rate helps matching fiber growth with its intrinsic relaxation behavior and relaxation time. That is, a lower expansion rate at a low expansion temperature will have an equivalent effect as a higher expansion rate at a high expansion temperature.

Example 8

In this Example, tubing was prepared with pigment-pretreated PTFE material using the methods described herein.

Figure 21A:
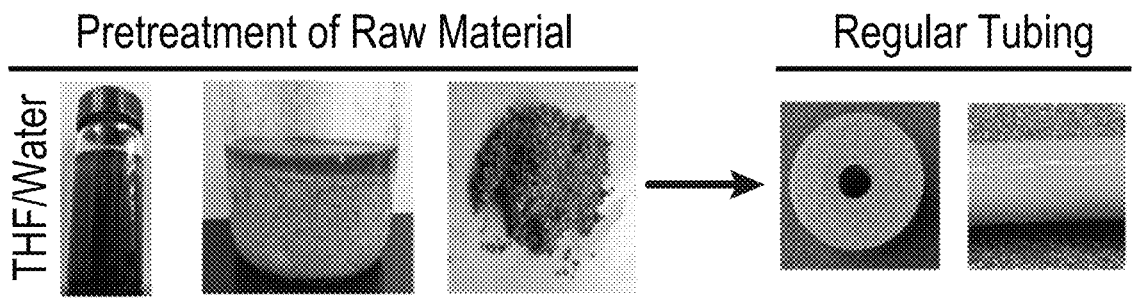
FIG. 21A depicts tubing with pigment-pretreated PTFE material as prepared in Example 8.
Figure 21B:
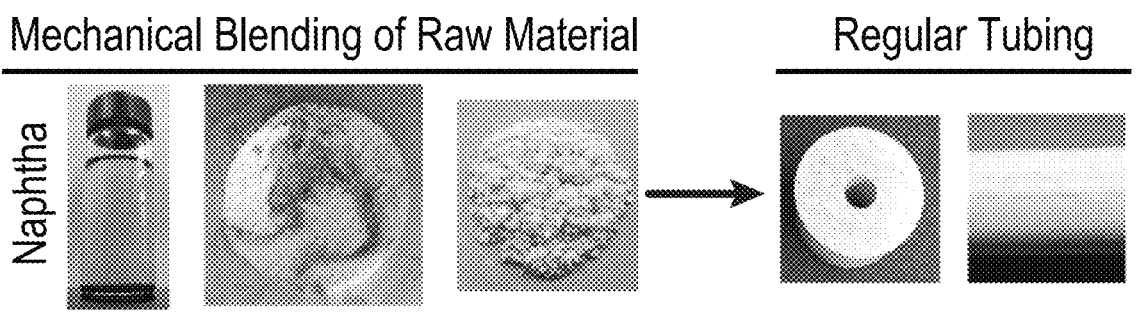
FIG. 21B depicts tubing with mechanically blended pigment and PTFE material as used as the control in Example 8.

Briefly, as shown in FIG. 21A, 0.5 wt % target material (i.e., pigment) was dissolved in a tetrahydrofuran (THF)/water solvent mixture, followed by immersing the PTFE raw material (i.e., powder) in the solvent mixture as described herein. After evaporation of the THF/water solvent mixture, all of the raw material was uniformly covered by the pigment. For comparison, mechanical blending of the same amount of pigment with the raw PTFE powder material was performed using a traditional lubricant (Naphtha). While this resulted in a uniformly blended mixture, the pigment barely dotted the PTFE material, let alone covered its surface, as shown in FIG. 21B.

Example 9

In this Example, ePTFE was pretreated with arginylglycylaspartic acid (RGD) using the methods of the present disclosure and then the biocompatibility of the ePTFE product including the RGD was analyzed and compared to untreated ePTFE.

1.4 grams RGD was dissolved in 12 grams water. Then, the yielding solution was added to 28 grams tetrahydrofuran (THF). Next, the RGD/water/THF mixture was added to 80 grams PTFE powder and rolling blended for 1 hour with a speed of 4 rpm. Eventually, the yielding PTFE raw material was placed in a ventilated place (room temperature, normal atmosphere) in order to let the water and THF evaporate. After complete evaporation, the pretreatment was finished. In the evaporation process, proper heating and vacuuming may speed up the evaporation.

Figures 22A, 22B:
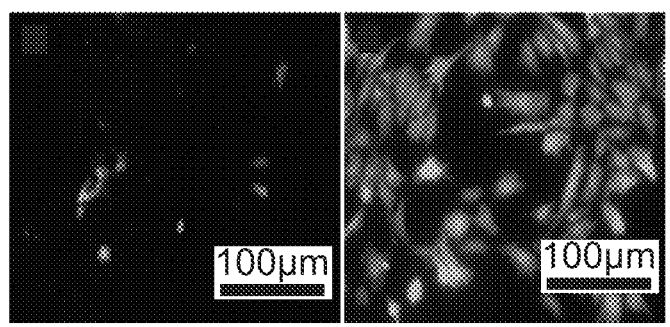
FIGS. 22A & 22B depict endothelial cell growth on (FIG. 22A) a pure ePTFE surface and (FIG. 22B) a pretreated ePTFE surface loaded with arginylglycylaspartic acid (RGD).

As shown in FIGS. 22A & 22B, drug-loaded ePTFE exhibited a greatly enhanced biocompatibility as compared to the untreated ePTFE, which makes this method outstanding for use in the medical and food industries.

Example 10

In this Example, PTFE was pretreated with sasilin, which is an anticoagulant and anti-inflammatory, using the methods of the present disclosure and then the biocompatibility of the resulting product was analyzed.

1.2 grams sasilin was dissolved in 12 grams water. Then, 28 grams dimethyl sulfoxide (DMSO) was added to a sasilin/water solution. Next, the resulting solution was rolling blended with 80 grams PTFE for 1 hour with a speed of 5 rpm. Eventually, vacuuming was applied to the yielding PTFE mixture, which allowed for fast evaporation of water and DMSO. The complete evaporation of water and DMSO resulted in a sasilin-loaded PTFE raw material.

Figures 23A, 23B:
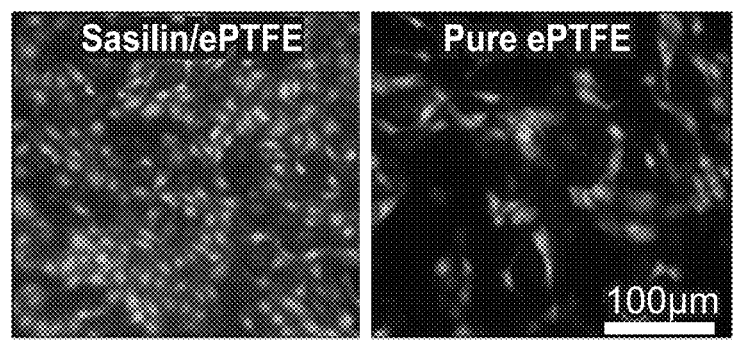
FIGS. 23A & 23B depict cell affinity to (FIG. 23A) a pretreated ePTFE surface loaded with sasilin and to (FIG. 23B) a pure ePTFE surface.

As shown in FIG. 23, sasilin loaded PTFE material exhibited a greatly improved cell affinity, which makes it much more appealing in medical applications.

What is claimed is:

1. A process for preparing an extruded product, the process comprising:
   blending a polytetrafluoroethylene (PTFE) powder with a lower alkyl ($C_1$-$C_{10}$) alcohol to form a blend, wherein the lower alkyl ($C_1$-$C_{10}$) alcohol is present in the blend in an amount of from about 10% by weight to about 30% by weight;
   preforming the blend;
   extruding the preformed blend to form a product; and
   evaporating the lower alkyl ($C_1$-$C_{10}$) alcohol from the extruded product.

2. The process as set forth in claim 1, wherein the lower alkyl ($C_1$-$C_{10}$) alcohol is a biocompatible lower alkyl ($C_1$-$C_{10}$) alcohol selected from the group consisting of methanol, ethanol, isopropanol, and combinations thereof.

3. The process as set forth in claim 2, wherein the biocompatible lower alkyl ($C_1$-$C_{10}$) alcohol is ethanol.

4. The process as set forth in claim 1, wherein the lower alkyl ($C_1$-$C_{10}$) alcohol is further mixed with water before blended with the PTFE powder and the alcohol/water mixture has a weight ratio of alcohol:water of from about 10:90 to about 100:0.

5. The process as set forth in claim 1, wherein blending comprising rolling the PTFE powder and lower alkyl ($C_1$-$C_{10}$o) alcohol for a period of from about 30 minutes to about 120 minutes.

6. The process as set forth in claim 5 further comprising aging the blend for a period of from about 30 minutes to about 48 hours after rolling.

7. The process as set forth in claim 1 comprising preforming the blend at a pressure of from about 1 MPa to about 30 MPa.

8. The process as set forth in claim 1, wherein evaporating of the lower alkyl ($C_1$-$C_{10}$) alcohol comprises heating the extruded product to a temperature of from 60° C. to about 200° C. for a period of from about 0.5 minutes to about 120 minutes.

9. The process as set forth in claim 1 further comprising sintering the heated extruded product at a temperature of from about 360° C. to about 400° C. for a period of from about 10 seconds to about 10 minutes.

10. The process as set forth in claim 1 further comprising expanding the extruded product.

11. The process as set forth in claim 9, wherein the expanding is conducted at a temperature of from about 25° C. to about 340° C.

12. The process as set forth in claim 9, wherein the extruded product is expanded at a rate of from about 1 mm/min to about 1000 mm/min.

13. The process as set forth in claim 9, wherein the extruded product is expanded at an expansion ratio of from about 100% to about 800%.

14. The process as set forth in claim 4 further comprising dissolving a target material in the lower alkyl ($C_1$-$C_{10}$) alcohol.

15. A medical implant comprising the extruded product made by the process of claim 1.

16. The medical implant as set forth in claim 15 selected from the group consisting of vascular grafts, cardiovascular and soft tissue patches, facial implants, surgical sutures, and endovascular prostheses.

17. A process for preparing an extruded product, the process comprising:
    mixing a lower alkyl ($C_1$-$C_{10}$) alcohol with water wherein the alcohol/water mixture has a weight ratio of alcohol:water of from about 10:90 to about 100:0;
    blending a polytetrafluoroethylene (PTFE) powder with the alcohol/water mixture to form a blend;
    preforming the blend;
    extruding the preformed blend to form a product; and
    evaporating the lower alkyl ($C_1$-$C_{10}$) alcohol from the extruded product.

* * * * *